United States Patent [19]
Gakic et al.

[11] Patent Number: 5,145,678
[45] Date of Patent: Sep. 8, 1992

[54] METHOD OF REDUCING BLOOD SERUM CHOLESTEROL

[76] Inventors: Dusko Gakic; Mileva Gakic, both of 15139 Leadwell St., Van Nuys, Calif. 91405

[21] Appl. No.: 643,608
[22] Filed: Jan. 22, 1991
[51] Int. Cl.$^5$ ............................................. A61K 35/78
[52] U.S. Cl. ................................. 424/195.1; 514/824
[58] Field of Search ...................... 424/195.1; 514/824

[56] References Cited

U.S. PATENT DOCUMENTS

| | | | |
|---|---|---|---|
| 3,203,862 | 8/1965 | Jones | 514/78 |
| 3,590,057 | 6/1971 | Suzuki | 514/824 |
| 3,957,976 | 5/1976 | Sugimoto | 514/53 |
| 4,398,721 | 8/1983 | McKay | 273/249 |
| 4,603,142 | 7/1986 | Burger et al. | 514/456 |
| 4,789,664 | 12/1988 | Seligson et al. | 514/23 |
| 4,810,827 | 3/1989 | Mitsuhashi et al. | 514/53 |
| 4,812,444 | 3/1989 | Mitsuhashi et al. | 514/53 |
| 4,826,825 | 5/1989 | Mitsuhashi et al. | 514/53 |
| 4,843,098 | 6/1989 | Shaw et al. | 514/778 |
| 4,851,392 | 7/1989 | Shaw et al. | 514/53 |
| 4,857,326 | 8/1989 | Stitt | 424/195.1 |
| 4,895,723 | 1/1990 | Amer et al. | 424/79 |

*Primary Examiner*—John W. Rollins
*Attorney, Agent, or Firm*—John J. Posta, Jr.

[57] ABSTRACT

The method of lowering human blood serum cholesterol consists of ingesting or administering to a patient orally once daily before any food intake a mixture of beet juice, lemon juice and bee honey. The mixture is in the proportions of about 1 part by volume of the beet juice, about 1 part by volume of the lemon juice and about 0.4 part by volume of the bee honey, and the total volume of the mixture is about 3.5 ounces. This regimen is carried out until the blood serum cholesterol drops to a safe level, below about 240 mg.dl. The length of time of administration depends on initial cholesterol level. However, in most cases, the treatment period is about 10-17 days. The mixture can be periodically administered thereafter to keep the cholesterol low or to again bring it down.

5 Claims, No Drawings

METHOD OF REDUCING BLOOD SERUM CHOLESTEROL

BACKGROUND OF THE INVENTION

1. Field of the Invention

The present invention generally relates to a medicinal composition and more particularly to an ingestible mixture which substantially reduces blood serum cholesterol and triglycerides.

2. Prior Art

Various types of foods are known to have some at least slightly favorable effect on blood serum cholesterol levels and levels of triglycerides. For example, fibers in a diet tend to slightly reduce cholesterol, if only by promoting rapid elimination and allowing less fat-absorption time and also by acting as a non-cholesterol-containing inert filler. Elimination of fats from the diet is useful in reducing cholesterol levels, as is reducing the overall level of fats and oils of all types, particularly those of the mono-unsaturated type. However, in many cases, the physician must resort to powerful drugs which have potentially dangerous side effects in order to substantially reduce cholesterol levels. For example, Niacin in large dosages has been suggested but is potentially damaging to the liver and produces so-called "hot flashes". Fatty acid amides have been tried (see U.S. Pat. No. 3,590,057) as have maltitol and lactitol (see U.S. Pat. No. 3,957,976). Cholestyramine has been used (see U.S. Pat. No. 4,895,723). However, their side effects are not well understood and thus they are potentially dangerous to employ.

There remains a need for a safe method of substantially reducing serum cholesterol, preferably using natural, harmless ingestible food ingredients which are readily available, inexpensive and effective, and which have no deleterious side effects. Such ingredients should be easy to ingest and be pleasant tasting, so as to encourage their use.

SUMMARY OF THE INVENTION

The improved method of the present invention satisfies all the foregoing needs. The method is substantially as set forth in the Abstract of the Disclosure.

In accordance with the method of the present invention, a mixture of beet juice, lemon juice and bee honey is ingested or administered orally once daily in the morning before any food intake, in an effective amount of about 3.5 fluid ounces, for a period of usually 15-20 days until the blood serum cholesterol level is substantially reduced. Preferably, the mixture is in the proportions of about one part by volume of the beet juice, an about equal volume of lemon juice and about 0.4 parts by volume of bee honey. The regimen is continued until the cholesterol level at least drops to a safe level below about 200 mg/dl. There is also a corresponding reduction in the triglyceride level.

The mixture is simple, inexpensive, small in quantity and highly palatable. It has no undesired side effects. It can be made up in quantity from off-the-shelf ingredients which must stored in a refrigerator for the period of the treatment. The method can be continued any desired length of time and can be reinstituted as needed to bring cholesterol levels back under control if they rise after the treatment has stopped. Further features of the method of the present invention are set forth in the following detailed description.

DETAILED DESCRIPTION

The improved method of the present invention comprises ingesting or administering orally to a human a mixture of beet juice, lemon juice and bee honey once daily in the morning before taking any other food or drink for a period of time sufficient to reduce the blood serum cholesterol of the ingestor a significant amount. The mixture comprises about 3-4 ounces, preferably about 3.5 fluid ounces of about 1 part by volume of beet juice, about 1 part by volume of lemon juice and about 0.4 parts by volume of bee honey. It will be understood that slightly different proportions can also be used in the mixture. For example, the lemon juice can be reduced to about 0.8 parts and the bee honey increased to about 0.6 parts by volume.

The beet juice is from the bulbous root of the sugar beet and is largely carbohydrate, including sucrose. The lemon juice is preferably unpreserved and preferably freshly squeezed juice from the common citrus lemon and, although acidic, is also largly carbohydrate. The bee honey of any conventional type, e.g., clover honey and is largely sugar, but like the beet juice and lemon juice, contains small amounts of other efficacious edible materials.

It is not known how the above-described mixture of carbohydrates in solution can work to lower blood serum cholesterol, particularly since it is taken in relatively small doses. However, that desired cholesterol-lowering effect has been clearly demonstrated. Triglycerides levels are also lowered. The effect created is described in the following specific Example.

EXAMPLE I

A female human patient having a high cholesterol blood serum level was first tested to determine the exact level of cholesterol. The results were as follows:

| | | |
|---|---|---|
| Cholesterol | 375 mg./dl. | high risk range |
| Triglycerides | 818 mg./dl. | |
| HDL | 39 mg./dl. | |

The patient then orally ingested 3.5 fluid ounces of the following mixture once daily for 17 days in the morning before eating or drinking anything else:

| MIXTURE | |
|---|---|
| beet juice | 1 part |
| lemon juice | 1 part |
| bee honey | 0.4 part |

The diet of the patient otherwise remained the same as before the 17 day period. At the end of the 17 day period, the blood serum of the patient was again tested, with the following results:

| | | |
|---|---|---|
| Cholesterol | 231 mg./dl. | borderline normal range |
| Triglycerides | 310 mg./dl. | |
| HDL | 35 mg./dl. | |

From the above, it can be seen that in 17 days using the above-described mixture, the patients cholesterol count dropped from 375 mg/dl. to 231 mg./dl. and that her triglyceride level dropped from 818 mg./dl. to 310 mg./dl., despite the fact that only 3.5 ounces of the mixture was imbibed each day. The HDL remained about the same. These were dramatic results. It will be readily appreciated that the mixture contained no ingredients which could produce undesirable side effects, was administered in very low amounts and was palatable. Accordingly, the method is efficacious.

EXAMPLE II

A second female human patient having a high cholesterol blood serum level was first tested to determine the exact level of cholesterol. The results were as follows:

| Cholesterol | 315 mg./dl. | high risk range |
|---|---|---|
| Triglycerides | 119 mg./dl. | |
| HDL | 5 mg./dl. | |

The patient then orally ingested 3.5 fluid ounces of the following mixture once daily for 17 days in the morning before eating or drinking anything else.

| MIXTURE | |
|---|---|
| beet juice | 1 part |
| lemon juice | 1 part |
| bee honey | 0.4 part |

The diet of the patient otherwise remained the same as before the 17 day period. At the end of the 17 day period, the blood serum of the patient was again tested, with the following results:

| Cholesterol | 258 mg./dl. | borderline normal range |
|---|---|---|
| Triglycerides | 101 mg./dl. | |
| HDL | 42 mg./dl. | |

From the above, it can be seen that in 17 days using the above-described mixture, the patients cholesterol count dropped from 315 mg./dl. to 231 mg./dl. and that her triglyceride level dropped from 119 mg./dl. to 101 mg./dl., despite the fact that only 3.5 fluid ounces of the mixture was imbibed each day.

Various modifications, changes, alterations and additions in the improved method of the present invention, its components, steps and parameters can be made. All such changes, modifications, alterations and additions as are within the scope of the appended claims form part of the present invention.

What is claimed is:

1. An improved method of treating hypercholesterolemia in humans in need of instant treatment to reduce human serum cholesterol, said method comprising:
    a) ingesting orally a mixture of beet juice, lemon juice, and bee honey once daily for a period of time sufficient to reduce serum cholesterol, and
    b) wherein said mixture weighs about 3.5 fluid ounces and has the proportions of about 1 part by volume of beet juice, about 1 part by volume of lemon juice, and about 0.4 parts by volume of bee honey.

2. The improved method of claim 1 wherein said period of time is sufficient to reduce said serum cholesterol to below about 240 mg./dl.

3. The improved method of claim 1 wherein said period of time is about 15-20 days and wherein said mixture is ingested in the morning before breakfast.

4. The improved method of claim 1 wherein said mixture weighs 3.5 fluid ounces and is 1 part by volume of beet juice, 1 part by volume of lemon juice and 0.4 part by volume of bee honey, wherein said period of time is 17 days and wherein said mixture is ingested only in the morning before any food or drink intake.

5. A pharmaceutical composition for treating hypercholesterolemia in humans in need of instant treatment to reduce human serum cholesterol comprising beet juice, lemon juice and bee honey, and wherein said mixture weighs about 3.5 fluid ounces and has the proportions of about 1 part by volume of beet juice, about 1 part by volume of lemon juice, and about 0.4 parts by volume of bee honey.

* * * * *